United States Patent
Riondel et al.

(10) Patent No.: US 6,632,957 B2
(45) Date of Patent: Oct. 14, 2003

(54) PROCESS FOR THE PREPARATION OF (DIALKYLPHOSPHONO)ALKYL (METH) ACRYLATE

(75) Inventors: Alain Riondel, Forbach (FR); Rosangela Pirri, Monterdon (FR); Thomas Jeanmaire, Bouzigues (FR)

(73) Assignee: Atofina, Paris la Defense Cedex (FR)

( * ) Notice: Subject to any disclaimer, the term of this patent is extended or adjusted under 35 U.S.C. 154(b) by 0 days.

(21) Appl. No.: 10/038,234

(22) Filed: Oct. 23, 2001

(65) Prior Publication Data

US 2003/0023107 A1 Jan. 30, 2003

(30) Foreign Application Priority Data

Oct. 24, 2000 (FR) .............................. 00 13618

(51) Int. Cl.$^7$ .................................................. C07F 9/02
(52) U.S. Cl. ....................................................... 558/87
(58) Field of Search ........................................... 558/87

(56) References Cited

U.S. PATENT DOCUMENTS 3,780,146 A * 12/1973 Gohborn et al.

FOREIGN PATENT DOCUMENTS

| DE | 2 127 821 | 12/1972 |
|----|-----------|---------|
| EP | 0 165 203 | 12/1985 |
| FR | 1 287 187 | 7/1962 |

OTHER PUBLICATIONS

N. Moszner et al., "Monomers for Adhesive Polymers, 2 Synthesis and Radical Polymerization of Hydrolytically Stable Acrylic Phosphonic Acids", vol. 200, No. 5, May 1999, pp. 1062–1067.

French International Search Report dated Jul. 2, 2001 for FR 00 13618.

* cited by examiner

Primary Examiner—Joseph K. McKane
Assistant Examiner—Robert Shiao
(74) Attorney, Agent, or Firm—David F. Ries; Clifford Chance US LLP

(57) ABSTRACT

The invention relates to a process allowing the preparation of a (dialkylphosphono)alkyl (meth)acrylate, corresponding to the formula:

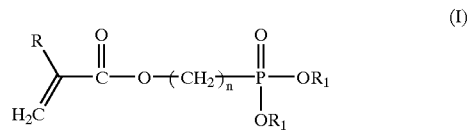

(I)

by reaction of an alkyl (meth)acrylate A of formula:

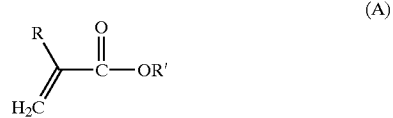

(A)

with a dialkylphosphonated alcohol B of formula:

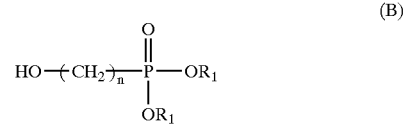

(B)

in the presence of a catalyst comprising zirconium acetylacetonate.

12 Claims, No Drawings

PROCESS FOR THE PREPARATION OF (DIALKYLPHOSPHONO)ALKYL (METH) ACRYLATE

The present invention relates to a process allowing the preparation of a (dialkylphosphono)alkyl (meth)acrylate, in particular of (dimethylphosphono)ethyl methacrylate.

American Patent U.S. Pat. No. 3,030,347 relates to copolymers based on dialkylphosphonoalkyl (meth)acrylate and a monomer which can be copolymerized with this compound. The dialkylphosphonoalkyl (meth)acrylate is prepared by addition of an alkyl phosphite C to an aldehyde, followed by reaction with (meth)acroyl chloride.

This latter reagent has the disadvantage of not being available on the industial scale and of generating significant amounts of effluents during its use.

There is therefore presently no process allowing (dialkylphosphono)alkyl (meth)acrylates to be prepared in a satisfactory manner on the industrial scale with a view, especially, to using them in industrial polymerization processes.

An object of the present invention is therefore a process for the preparation of (dialkylphosphono)alkyl (meth) acrylate which can easily be employed on the industrial scale.

More precisely, a first object of the present invention is a process for the preparation of a (dialkylphosphono)alkyl (meth)acrylate corresponding to the formula:

$$\underset{H_2C}{\overset{R}{>}}C=C\overset{O}{\underset{\|}{-}}O-(CH_2)_n-\overset{O}{\underset{\underset{OR_1}{|}}{P}}-OR_1 \quad (I)$$

in which:
R is a hydrogen or a methyl group
$R_1$ is an alkyl group having from 1 to 6 carbon atoms, especially 1 or 2 carbon atoms;
n is an integer from 1 to 3.

This process comprises the reaction of an alkyl (meth) acrylate A of formula $$\underset{H_2C}{\overset{R}{>}}C=C\overset{O}{\underset{\|}{-}}OR' \quad (A)$$

in which:
R is a hydrogen atom or a methyl group;
R' is an alkyl group having from 1 to 4 carbon atoms with a dialkylphosphonated alcohol B of formula:

$$HO-(CH_2)_n-\overset{O}{\underset{\underset{OR_1}{|}}{P}}-OR_1 \quad (B)$$

in which $R_1$ and n have the meanings given above.

Such a process therefore has the advantage of resorting to a transesterification, which avoids requiring products which are not very available in the trade or with high toxicity. In addition, it allows (dialkylphosphono)alkyl (meth)acrylates to be prepared at low cost.

A second object of the present invention is a polymerization process in which the phosphonated monomer obtained by the preparation process according to the invention is polymerized with at least one $C_1$ to $C_4$ alkyl (meth)acrylate.

According to a preferred embodiment of the polymerization process of the invention, the phosphonated monomer is employed during the polymerization in the form of a solution of this monomer in the alkyl (meth)acrylate A which has served for its preparation.

Other characteristics and advantages of the invention will now be described in detail in the account which follows, and illustrated by the appended figure which represents the apparatus used for carrying out the process according to the invention.

Preparation of the (Dialkylphosphono)Alkyl (Meth) Acrylate

1) Reagents

Alkyl (meth)acrylate A

According to the invention, the starting material used is an alkyl (meth)acrylate A of formula:

$$\underset{H_2C}{\overset{R}{>}}C=C\overset{O}{\underset{\|}{-}}OR' \quad (A)$$

in which:
R is a hydrogen atom or a methyl group;
R' is an alkyl group having from 1 to 4 carbon atoms.
Preferably, the group R is the methyl group and the group R' is the methyl or ethyl, especially methyl, group.
As alkyl (meth)acrylate A, mention can therefore be made of methyl, ethyl, propyl, butyl acrylates and methyl, ethyl, propyl and butyl methacrylates.

The alkyl (meth)acrylate A is therefore reacted with the dialkylphosphonated alcohol B.

Dialkylphosphonated alcohol B

This compound has the formula:

$$HO-(CH_2)_n-\overset{O}{\underset{\underset{OR_1}{|}}{P}}-OR_1 \quad (B)$$

in which
$R_1$ is an alkyl group having from 1 to 6 carbon atoms; and
n is an integer from 1 to 3.
Preferably, $R_1$ contains 1 to 3 carbon atoms. More preferentially, $R_1$ is a methyl or ethyl group.

To obtain a dialkylphosphonated alcohol B in which n is 2 or 3, a free-radical reaction is carried out, in a conventional manner, between an alkyl phosphite C of formula:

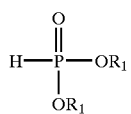

in which $R_1$ has the meaning given above,
and an unsaturated ester D of formula

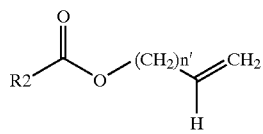

in which
$R_2$ is an alkyl group containing from 1 to 4 carbon atoms, preferably a methyl,
n' is 0 or 1;
then the intermediate E obtained, of formula:

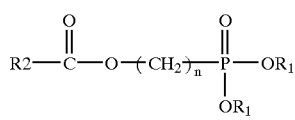

in which:
$R_1$, $R_2$ have the meanings indicated above
n is 2 or 3;
is saponified to result in the dialkylphosphonated alcohol B.

To obtain a dialkylphosphonated alcohol B in which n is 1, an alkyl phosphite C is reacted in a conventional manner with formaldehyde.

2) Reaction of the Alkyl (Meth)Acrylate A with the Dialkylphosphonated Alcohol B This reaction is a transesterification reaction. It is therefore carried out under the conditions customary for transesterification reactions, which are well known to the person skilled in the art.

The temperatures employed are in general from 85° C. to 130° C., preferably from 95° C. to 120° C.

The ratio of the reagents, namely (meth)acrylic ester A: phosphonated alcohol B varies within large limits, for example between 1.4 and 5, preferably between 2 and 4.

Preferably, the reaction is carried out in the presence of a catalyst, in a quantity of between $10^{-4}$ and $10^{-1}$, preferably between $5.10^{-4}$ and $5.10^{-2}$, mol/mol of alcohol.

As catalyst, zirconium acetylacetonate is preferentially used.

(Dialkylphosphono)Alkyl (Meth)Acrylate Monomer

The final product, namely the (dialkylphosphono)alkyl (meth)acrylate monomer, can serve for the preparation of textile binders having a nonflammable character.

Its insensitivity to hydrolysis can also be turned to good account by producing aqueous dispersions useful as paint binders for metals.

It can also be used in order to prepare polymers of low mass which can be employed as dispersants for fillers.

It finds particularly interesting applications in the manufacture of latexes, because it confers to the latter properties of adhesion to metals or anti-corrosion properties, although the anti-corrosion properties are normally obtained by means of chromium atoms.

EXAMPLE

The following example is given in a uniquely illustrative capacity and does not have any limiting character.

Synthesis of the Dimethylphosphonoethyl Methacrylate

Into a 0.5 l double-jacket glass reactor equipped with a variable speed mechanical stirrer (4-bladed screw), a probe for the measurement of the temperature, a descending tube for the introduction of air and an adiabatic distillation column at the top (of Vigreux type—3 theoretical plates), this column itself having a reflux head at the top, are introduced 154.1 g (1 mol) of dimethylphosphonoethanol, 400 g (4 mol) of methyl methacrylate, 0.1333 g of EMHQ stabilizer and 4.87 g of $Zr(acac)_4$.

The reactor is heated by means of a thermostated oil bath.

The assembly operates under reduced pressure owing to the vacuum produced by a vane pump.

A thermometer measures the column head temperature.

An appropriate device allows the R/D (reflux/draw-off) ratio to be controlled at the column head.

The different fractions are collected in a 250 ml receiver.

In a first step, the reagents are dried under the following conditions:

Temperature in the reactor: 60° C.
Temperature at the column head: 60° C.
Pressure: 200 mbar
R/D: 5/1
Duration of the operation: 15 minutes
Mass drawn off: 100 g In a second step, the reaction proper is carried out under the following conditions:

Temperature in the reactor: 110° C. maximum
Temperature at the column head: 35–60° C.
Pressure: increasing from 350 to 780 mbar
RID: 5/1
Duration of the operation: 4 hours
Mass drawn off: 110.1 g In a third step, the excess of methyl methacrylate is eliminated under the following conditions:

Temperature in the reactor: 110° C. maximum
Pressure: decreasing from 780 to 50 mbar
Duration of the operation: 1 hour
Mass drawn off: 122 g The overall yield is 94% of dimethylphosphonoethyl methacrylate which is present in the form of a clear transparent yellow liquid whose purity determined by NMR is 95%.

What is claimed is:
1. Process for the preparation of a (dialkylphosphono) alkyl (meth)acrylate corresponding to the formula:

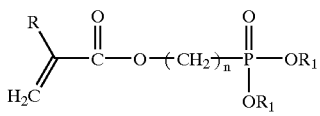 (I)

in which:
R is a hydrogen or a methyl group
$R_1$ is an alkyl group having 1 to 6 carbon atoms
n is an integer from 1 to 3;
comprising the reaction of an alkyl (meth)acrylate A of formula

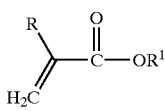 (A)

in which:
R is a hydrogen atom or a methyl group;
$R_1$ is an alkyl group having from 1 to 4 carbon atoms
with a dialkylphosphonated alcohol B of formula:

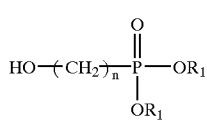 (B)

in which $R_1$ and n have the meanings given above;
in the presence of a catalyst comprising zirconium acetylacetonate.

2. Process according to claim 1, in which the dialkylphosphonated alcohol B in which n is equal to 1 is prepared by reaction of an alkyl phosphite C of formula:

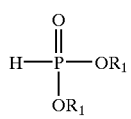 (C)

in which $R_1$ has the same meaning as above;
with formaldehyde.

3. Process according to claim 1, in which $R_1$ contains from 1 to 3 carbon atoms.

4. Process according to claim 1, in which R is the methyl group.

5. Process according to claim 1, in which R' is the methyl or ethyl group.

6. Process according to claim 1, in which
$R_1$ contains from 1 to 3 carbon atoms;
R is the methyl group; and
R' is the methyl or ethyl group.

7. Process according to claim 1, in which the reaction of the alkyl (meth)acrylate A with the dialkylphosphonated alcohol B is carried out at a temperature of 85° C. to 130° C., preferably of 95° C. to 120° C.

8. Process according to claim 1, in which the reaction of the alkyl (meth)acrylate A with the dialkylphosphonated alcohol B is carried out in accordance with a (meth)acrylic ester A: phosphonated alcohol B ratio of between 1.4 and 5 and preferably of between 2 and 4.

9. Process according to claim 6, in which the reaction of the alkyl (meth)acrylate A with the dialkylphosphonated alcohol B is carried out at a temperature of 85° C. to 130° C., preferably of 95° C. to 120° C.

10. Process according to claim 6, in which the reaction of the alkyl (meth)acrylate A with the dialkylphosphonated alcohol B is carried out in accordance with a (meth)acrylic ester A: phosphonated alcohol B ratio of between 1.4 and 5 and preferably of between 2 and 4.

11. Process according to claim 7, in which the reaction of the alkyl (meth)acrylate A with the dialkylphosphonated alcohol B is carried out in accordance with a (meth)acrylic ester A: phosphonated alcohol B ratio of between 1.4 and 5 and preferably of between 2 and 4.

12. Process according to claim 8, in which the reaction of the alkyl (meth)acrylate A with the dialkylphosphonated alcohol B is carried out in accordance with a (meth)acrylic ester A: phosphonated alcohol B ratio of between 1.4 and 5 and preferably of between 2 and 4.

* * * * *

UNITED STATES PATENT AND TRADEMARK OFFICE
CERTIFICATE OF CORRECTION

PATENT NO.     : 6,632,957 B2
DATED          : October 14, 2003
INVENTOR(S)    : Alain Riondel et al.

It is certified that error appears in the above-identified patent and that said Letters Patent is hereby corrected as shown below:

Column 5,
Line 17, "$R^{1}$" should read -- $R'$ --.
Line 24, "$R_1$" should read -- $R'$ --.

Signed and Sealed this

Thirtieth Day of December, 2003

JAMES E. ROGAN
*Director of the United States Patent and Trademark Office*